(12) United States Patent
Shen et al.

(10) Patent No.: US 11,274,153 B2
(45) Date of Patent: Mar. 15, 2022

(54) ANTI-PD-L1 NANOBODY AND USE THEREOF

(71) Applicant: INNOVENT BIOLOGICS (SUZHOU) CO., LTD., Jiangsu (CN)

(72) Inventors: Xiaoning Shen, Jiangsu (CN); Xiaoniu Miao, Jiangsu (CN); Xiaolin Liu, Jiangsu (CN)

(73) Assignee: INNOVENT BIOLOGICS (SUZHOU) CO., LTD., Jiangsu (CN)

( * ) Notice: Subject to any disclaimer, the term of this patent is extended or adjusted under 35 U.S.C. 154(b) by 781 days.

(21) Appl. No.: 16/068,815

(22) PCT Filed: Aug. 3, 2017

(86) PCT No.: PCT/CN2017/095884
§ 371 (c)(1),
(2) Date: Jul. 9, 2018

(87) PCT Pub. No.: WO2018/024237
PCT Pub. Date: Feb. 8, 2018

(65) Prior Publication Data
US 2019/0023793 A1    Jan. 24, 2019

(30) Foreign Application Priority Data

Aug. 4, 2016 (CN) .................. 201610634596.X

(51) Int. Cl.
| | | |
|---|---|---|
| C07K 16/28 | (2006.01) |
| A61P 35/00 | (2006.01) |
| A61K 39/395 | (2006.01) |
| A61K 51/10 | (2006.01) |
| C12N 15/85 | (2006.01) |
| A61K 47/68 | (2017.01) |
| G01N 33/574 | (2006.01) |
| A61K 39/00 | (2006.01) |

(52) U.S. Cl.
CPC ........ *C07K 16/2827* (2013.01); *A61K 39/395* (2013.01); *A61K 47/6849* (2017.08); *A61K 51/10* (2013.01); *A61K 51/1027* (2013.01); *A61P 35/00* (2018.01); *C07K 16/28* (2013.01); *C12N 15/85* (2013.01); *G01N 33/574* (2013.01); *A61K 2039/505* (2013.01); *C07K 2317/22* (2013.01); *C07K 2317/24* (2013.01); *C07K 2317/565* (2013.01); *C07K 2317/567* (2013.01); *C07K 2317/569* (2013.01); *C07K 2317/76* (2013.01); *C07K 2317/92* (2013.01); *C07K 2317/94* (2013.01); *C07K 2319/30* (2013.01); *C07K 2319/61* (2013.01)

(58) Field of Classification Search
None
See application file for complete search history.

(56) References Cited

U.S. PATENT DOCUMENTS

| | | |
|---|---|---|
| 8,217,149 B2 | 7/2012 | Irving et al. |
| 8,741,295 B2 | 6/2014 | Olive et al. |
| 8,907,065 B2 | 12/2014 | Hermans et al. |
| 9,624,298 B2 | 4/2017 | Nastri et al. |
| 9,637,546 B2 | 5/2017 | Olive et al. |
| 9,920,123 B2 | 3/2018 | Irving et al. |
| 2010/0028341 A1 | 2/2010 | Hermans et al. |
| 2010/0203056 A1 | 8/2010 | Irving et al. |
| 2011/0129458 A1 | 6/2011 | Dolk et al. |
| 2011/0262427 A1 | 10/2011 | Hermans et al. |
| 2012/0039870 A9 | 2/2012 | Dolk et al. |
| 2012/0039906 A1 | 2/2012 | Olive et al. |
| 2013/0045200 A1 | 2/2013 | Irving et al. |
| 2013/0045201 A1 | 2/2013 | Irving et al. |
| 2013/0045202 A1 | 2/2013 | Irving et al. |
| 2014/0065135 A1 | 3/2014 | Irving et al. |
| 2014/0335093 A1 | 11/2014 | Olive et al. |
| 2014/0341917 A1 | 11/2014 | Nastri et al. |
| 2015/0266958 A1 | 9/2015 | Hermans et al. |
| 2015/0322153 A1 | 11/2015 | Irving et al. |
| 2016/0222117 A1 | 8/2016 | Irving et al. |
| 2016/0280786 A1 | 9/2016 | Hermans et al. |
| 2016/0289327 A1 | 10/2016 | Hermans et al. |
| 2017/0107287 A1 | 4/2017 | Irving et al. |
| 2017/0253653 A1 | 9/2017 | Nastri et al. |
| 2017/0253654 A1 | 9/2017 | Nastri et al. |

FOREIGN PATENT DOCUMENTS

| | | |
|---|---|---|
| CN | 101550191 A | 10/2009 |
| CN | 102245640 A | 11/2011 |
| CN | 106397592 A | 2/2014 |
| CN | 103987405 A | 8/2014 |
| CN | 104404630 A | 3/2015 |
| WO | 2008071447 A2 | 6/2008 |
| WO | 2010089411 A2 | 8/2010 |

OTHER PUBLICATIONS

Muyldermans et al. (ARB:82:775-97, 2013).*
International Search Report for PCT/CN2017/095884 dated Oct. 26, 2017.
Zhang, F. et al., "Structural Basis of a Novel PD-L1 Nanobody for Immune Checkpoint Blockade," Cell Discovery, Mar. 7, 2017, vol. 3, pp. 1-12.
Jiang, R. et al., "Application and the Research Progress of Nanobodies," Chemistry of Life, Dec. 31, 2013, vol. 33, No. 3, pp. 307-315.
Sheridan, C. et al., "Immune-Checkpoint Inhibitors March on, Now in Combinations," Nature Biotechnology, Apr. 30, 2014, vol. 32, No. 4, pp. 297-299.
English Absliact for CN106397592, Publication Date: Feb. 15, 2017.
English Abstract for CN104404630, Publication Date: Mar. 11, 2015.
English Abstract for CN101550191, Publication Date: Oct. 7, 2009.

* cited by examiner

*Primary Examiner* — Brad Duffy
(74) *Attorney, Agent, or Firm* — Millen, White, Zelano & Branigan, PC

(57) ABSTRACT

Disclosed is a nanobody against the human programmed death factor PD-LI. The antibody has the function of blocking the binding of PD-LI to the receptor PD-I. Disclosed are the nanobody and the gene sequence encoding the nanobody, the corresponding expression vector and the host cell capable of expressing the nanobody, and the method for producing the nanobody. At the same time, also disclosed is the sequence of the humanized PD-LI nanobody. The humanized nanobody still has the function of blocking the binding of PD-LI to PD-1, and has a relatively high affinity and a relatively good specificity.

11 Claims, 7 Drawing Sheets

Specification includes a Sequence Listing.

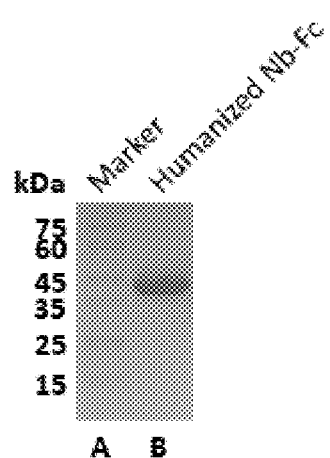
Fig 7
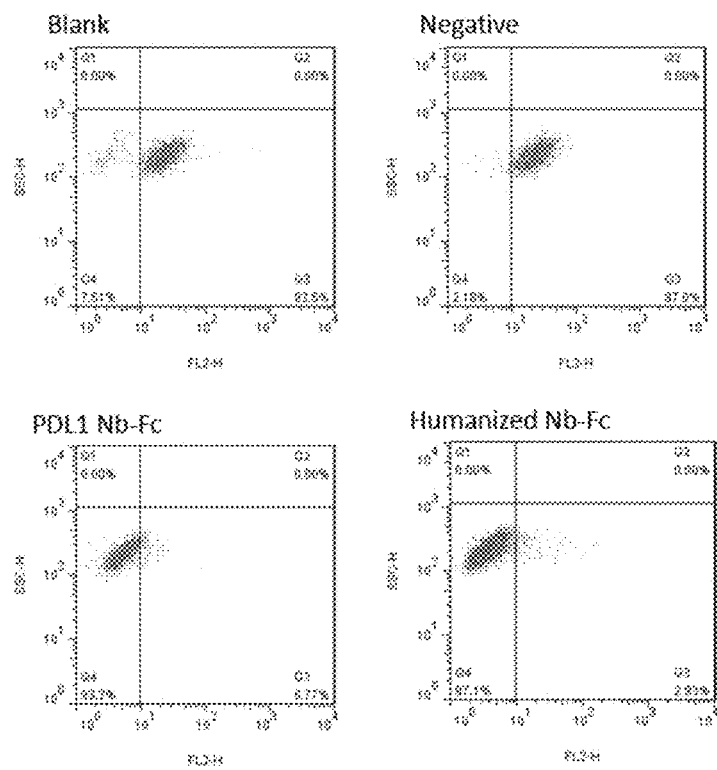
Fig 8
| Sample | Kon(M⁻¹s⁻¹) | Koff(s⁻¹) | KD(M) |
| --- | --- | --- | --- |
| Nb-Fc | $2.33 \times 10^5$ | $5.47 \times 10^{-4}$ | $2.34 \times 10^{-9}$ |
| Humanized Nb-Fc | $1.82 \times 10^5$ | $4.12 \times 10^{-4}$ | $2.26 \times 10^{-9}$ |
Fig 9

ANTI-PD-L1 NANOBODY AND USE THEREOF

TECHNICAL FIELD

The present disclosure relates to the field of biomedical or biopharmaceutical technology, and more specifically to the nanobodies against PD-L1, the coding sequences and the uses thereof.

BACKGROUND

Programmed death 1 ligand 1 (PD-L1), also known as CD274, is a member of the B7 family and is a ligand for PD-1. PD-L1 is a type I transmembrane protein with a total of 290 amino acids, including one IgV-like region, one IgC-like region, one transmembrane hydrophobic region, and one intracellular region composed of 30 amino acids.

Different from other B7 family molecules, PD-L1 has an effect of negative regulation on immune response. The study found that PD-L1 is mainly expressed in activated T cells, B cells, macrophages, dendritic cells and the like. In addition to lymphocytes, PD-L1 is also expressed in the endothelial cells of other tissues such as thymus, heart, and placenta, as well as in the non-lymphoid system such as melanoma, liver cancer, gastric cancer, renal cell carcinoma, ovarian cancer, colon cancer, breast cancer, esophageal cancer, head and neck cancer, etc. PD-L1 has an extensive effect on the regulation of autoreactive T, B cells and immune tolerance, and it plays a role in peripheral T and B cell responses. The high expression of PD-L1 on tumor cells correlates with the poor prognosis of cancer patients.

Programmed death-1 (PD-1) factor, which binds to PD-L1 and is also known as CD279, is a member of the CD28 family. It contains two tyrosine residues in the cytoplasmic region. One residue near to the N-terminus is located in the immunoreceptor tyrosine-based inhibitory motif (ITIM), and the other near to the C-terminal is located in the immunoreceptor tyrosine-based switch motif (ITSM). PD-1 is mainly expressed on the surface of activated T lymphocytes, B lymphocytes, and macrophages. Normally, PD-1 can inhibit the function of T lymphocytes, promote the function of Treg, thereby inhibiting the autoimmune response and preventing from the occurrence of autoimmune diseases. However, in the development of tumors, the binding of PD-L1 expressed by tumor cells and PD-1 can promote the immune escape of tumors through the inhibitory effect of lymphocytes. The binding of PD-L1 to PD-1 can lead to a variety of biological changes, causing immune regulation, such as inhibiting the proliferation and activation of lymphocytes, inhibiting the differentiation of CD4+ T cells into Th1 and Th17 cells, and inhibiting the release of inflammatory cytokines, etc.

The successful application of monoclonal antibodies in cancer detection and bio-targeted therapy has led to a revolution in the treatment of cancer. However, the molecular weight of the conventional monoclonal antibody (150 kD) is too large to allow the antibody to penetrate the tissue, resulting in a lower effective concentration in the tumor region and insufficient therapeutic effect. The immunogenicity of traditional antibodies is high while the modified antibody can hardly achieve the intrinsic affinity. In addition, a number of facts, such as the long development cycle, high production costs, and lacking of stability of fully humanized traditional antibodies, limit their application and popularity in clinical practice.

Nanobodies are the smallest antibody molecules so far, and their molecular weight is ⅒ that of ordinary antibodies. In addition to the antigen reactivity of monoclonal antibodies, nanobodies also possess unique functional properties such as low molecular weight, high stability, good solubility, easy expression, weak immunogenicity, strong penetration, and strong targeting, simple humanization, and low preparation cost, etc. It almost perfectly overcomes the shortcomings of traditional antibody, such as long development cycle, low stability, stringent conditions for storage, etc.

However, there is still a lack of satisfactory nanobodies against PD-L1 in the field. Therefore, it is an urgent need in the art to develop new specific nanobodies that are effective against PD-L1.

SUMMARY OF DISCLOSURE

The object of the present disclosure is to provide a class of specific nanobodies that are effective against PD-L1.

In the first aspect of the present disclosure, it provides a complementary determining region (CDR) of VHH chain of anti-PD-L1 nanobodies, said complementary determining region (CDR) of VHH chain is consisting of CDR1 as set forth by SEQ ID NO.: 5, CDR2 as set forth by SEQ ID NO.: 6 and CDR3 as set forth by SEQ ID NO.: 7.

In another preferred embodiment, said CDR1, CDR2 and CDR3 are separated by frame regions FR1, FR2, FR3, and FR4 of the VHH chain.

The second aspect of the present disclosure provides a VHH chain of anti-PD-L1 nanobodies, said VHH chain comprises a frame region (FR) and the complementary determining region (CDR) of the first aspect, and said frame region (a) is consisting of FR1 as set forth by SEQ ID NO.:1, FR2 as set forth by SEQ ID NO.: 2, FR3 as set forth by SEQ ID NO.: 3, and FR4 as set forth by SEQ ID NO.: 4; or (b) is consisting of FR1 as set forth by SEQ ID NO.:10, FR2 as set forth by SEQ ID NO.: 11, FR3 as set forth by SEQ ID NO.: 12, and FR4 as set forth by SEQ ID NO.: 13.

In another preferred embodiment, the VHH chain of said anti-PD-L1 nanobodies is as set forth by SEQ ID NO.: 8 or 14.

The third aspect of the present disclosure provides an anti-PD-L1 nanobody, which is an anti-PD-L1 nanobody against PD-L1 epitope, and has a VHH chain as set forth by the amino acid sequence of SEQ ID NO.: 8 or SEQ ID NO.: 14.

The fourth aspect of the present disclosure provides a polynucleotide, and said polynucleotide encodes a protein selected from the group consisting of the CDR of VHH chain of the anti-PD-L1 nanobodies according to the first aspect of the present disclosure, VHH chain of the anti-PD-L1 nanobodies according to the second aspect of the present disclosure, and the anti-PD-L1 nanobodies according to the third aspect of the present disclosure.

In another preferred embodiment, said polynucleotide has a nucleotide sequence of SEQ ID NO.: 9 or 15.

In another preferred embodiment, said polynucleotide includes DNA or RNA.

The fifth aspect of the present disclosure provides an expression vector, said expression vector comprises the polynucleotide according to the forth aspect of the present disclosure.

The sixth aspect of the present disclosure provides a host cell, and said host cell comprises the expression vector according to the fifth aspect of the present disclosure, or the polynucleotide according to the forth aspect of the present disclosure is integrated within genome of the host cell.

In another preferred embodiment, said host cell includes prokaryocyte or eukaryocyte.

In another preferred embodiment, said host cell is selected from the group consisting of *E. coli.* and yeast cells.

The seventh aspect of the present disclosure provides a method for producing anti-PD-L1 nanobodies comprising the steps of:

(a) culturing said host cell according to the sixth aspect of the present disclosure under a condition suitable for producing nanobodies, thereby obtaining a culture containing said anti-PD-L1 nanobodies; and (b) isolating or recovering said anti-PD-L1 nanobodies from said culture.

In another preferred embodiment, said anti-PD-L1 nanobody has an amino acid sequence of SEQ ID NO.: 8 or 14.

The eighth aspect of the present disclosure provides an immunoconjugate, and said immunoconjugate comprises:

(a) the VHH chain of said anti-PD-L1 nanobodies according to the second aspect of the present disclosure, or said anti-PD-L1 nanobodies according to the third aspect of the present disclosure; and (b) a conjugating part selected from the group consisting of a detectable marker, drug, toxin, cytokine, radionuclide, and enzyme.

In another preferred embodiment, said conjugating part is a drug or toxin.

In another preferred embodiment, said conjugating part is a detectable marker.

In another preferred embodiment, said conjugate is selected from the group consisting of fluorescent or luminescent markers, radiomarkers, MRI (magnetic resonance imaging) or CT (computed tomography) contrast agents, or enzymes, radionuclides, biotoxins, cytokines (eg, IL-2, etc.), antibodies, antibody Fc fragments, antibody scFv fragments, gold nanoparticles/nanorods, viral particles, liposomes, nanomagnetic particles, prodrug activating enzymes (eg, DT-diaphorase (DTD) or biphenyl hydrolase-like protein (BPHL), chemotherapeutic agents (eg, cisplatin) or any form of nanoparticles, etc. that produce detectable products.

In another preferred embodiment, said immunoconjugate contains multivalent (such as bivalent) VHH chains of the anti-PD-L1 nanobodies according to the second aspect of the present disclosure, or the anti-PD-L1 nanobodies according to the third aspect of the present disclosure.

In another preferred embodiment, said multivalent refers that the amino acid sequence of the immunoconjugate contains several repeated VHH chains of the anti-PD-L1 nanobodies according to the second aspect of the present disclosure, or the anti-PD-L1 nanobodies according to the third aspect of the present disclosure.

The ninth aspect of the disclosure provides a use of the anti-PD-L1 nanobodies according to the third aspect of the present disclosure for preparing (a) an agent for detecting PD-L1 molecule; or (b) a medicant for treating cancers.

In another preferred embodiment, said detecting comprises detection conducted by flow cytometry or cell immunofluorescence.

The tenth aspect of the disclosure provides a pharmaceutical composition comprising:

(i) the complementary determining region (CDR) of VHH chain of the anti-PD-L1 nanobodies according to the first aspect of the present disclosure, the VHH chain of the anti-PD-L1 nanobodies according to the second aspect of the present disclosure, the anti-PD-L1 nanobodies according to the third aspect of the present disclosure, or the immunoconjugate according to eighth aspect of the present disclosure; and (ii) a pharmaceutically acceptable carrier.

In another preferred embodiment, said pharmaceutical composition is in a form of injection.

In another preferred embodiment, said pharmaceutical composition is used for preparing a medicant for treating cancers, and said cancer is selected from the group consisting of gastric cancer, liver cancer, leukemia, renal tumor, lung cancer, small intestinal cancer, bone cancer, prostate cancer, colorectal cancer, breast cancer, colon cancer, prostate cancer, cervical cancer, lymphoma, adrenal tumor and bladder tumor.

The eleventh aspect of the present disclosure provides one or more use of the anti-PD-L1 nanobodies according to the third aspect of the present disclosure:

(i) for detecting human PD-L1 molecule;
(ii) for flow cytometry assay;
(iii) for cell immunofluorescence detection;
(iv) for treating cancer;
(v) for diagnosing cancer.

In another preferred embodiment, said use is non-diagnostic and non-therapeutic.

The twelfth aspect of the present disclosure provides a recombinant protein, and said recombinant protein has:

(i) the sequence of variable region of heavy chain VHH according to the second aspect of the present disclosure or the sequence of nanobodies according to the third aspect of the present disclosure; and (ii) an optional tag sequence assisting expression and/or purification.

In another preferred embodiment, said tag sequence includes 6His tag or HA tag.

In another preferred embodiment, said recombinant protein specifically binds to the PD-L1 protein.

The thirteenth aspect of the present disclosure provides a use of the VHH chain of the anti-PD-L1 nanobodies according to the second aspect of the present disclosure, the anti-PD-L1 nanobodies according to the third aspect of the present disclosure, or the immunoconjugate according to eighth aspect of the present disclosure for preparing a medicant, agent, detecting plate or kit;

wherein, said agent, detecting plate or kit is used for detecting PD-L1 protein in the testing sample;

wherein, said medicant is used for treating or preventing cancers expressing PD-L1 (i.e. PD-L1 positive).

In another preferred embodiment, said cancer comprises gastric cancer, lymphoma, liver cancer, leukemia, renal tumor, lung cancer, small intestinal cancer, bone cancer, prostate cancer, colorectal cancer, breast cancer, colon cancer, prostate cancer, or adrenal tumors.

The fourteenth aspect of the present disclosure provides a method for detecting PD-L1 protein in a sample, and said method comprises the steps of:

(1) contacting the sample with the nanobodies according to the third aspect of the present disclosure;

(2) detecting the antigen-antibody complex, wherein the detected complex indicated the presence of PD-L1 protein.

The fifteenth aspect of the present disclosure provides a method for treating a disease, said method comprising administering the nanobodies according to the third aspect of the present disclosure or the immunoconjugate according to the eighth aspect of the present disclosure to a subject in need.

In another preferred embodiment, said subject includes mammals, such as human.

The sixteenth aspect of the present disclosure provides a frame region (FR) of a VHH chain of an anti-PD-L1 nanobody, and said frame region (FR) of the VHH chain is composed of FR1 as set forth by SEQ ID NO.: 1, FR2 as set forth by SEQ ID NO.: 2, FR3 as set forth by SEQ ID NO.: 3, and FR4 as set forth by SEQ ID NO.: 4.

It is to be understood that within the scope of the present disclosure, the above-described technical features of the present disclosure and the technical features specifically described in the following (e.g., examples) may be combined with each other to form a new or preferred technical solution, which will not be repeated herein due to the limited space.

BRIEF DESCRIPTION OF THE FIGURES

FIG. 7 illustrates the humanized PD-L1 nanobodies by eukaryotic expression upon purification. Four kinds of humanized PD-L1 nanobodies are expressed by HEK293F cells, wherein A is the protein molecule as a standard, B is the humanized PD-L1 Nb protein coded by the amino acid sequence of SEQ ID NO.: 10. The expressed nanobody has an Fc-tag protein and the protein purity reaches over 90%.

FIG. 8 shows the blocking effects of humanized PD-L1 nanobodies tested by FACS. It is conducted by the co-reaction of EBC-1 cells naturally expressing PD-L1 protein, humanized nanobodies and biotinylated hPD-1-Fc protein. It shows that the binding rate of PD-1-Fc-biotin and EBC-1 cells in blank group and negative control group is over 90%, while after the PD-L1 nanobodies and humanized nanobodies are added, the binding rate of PD-1-Fc-biotin and EBC-1 cells is only less than 10%. This demonstrates the interaction between PD-1 and PD-L1 can be significantly blocked by the added nanobodies.

FIG. 9 shows the testing results of the affinity of PD-L1 nanobodies. The affinity of PD-L1 nanobodies is tested by BiaCore T200. It shows that the affinity before humanization is $2.34 \times 10^{-9}$ M and the affinity after humanization is $2.26 \times 10^{-9}$ M. Humanization does not affect the affinity of the nanobodies.

DETAILED DESCRIPTION

Figure 1:
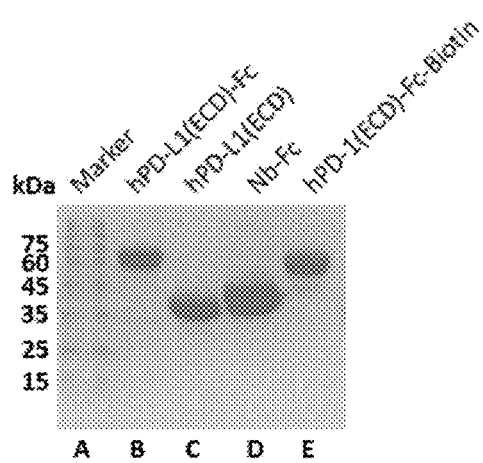
FIG. 1 shows the SDS-PAGE result of the purified antigen protein and nanobody, in which A is the nucleic acid molecule for reference, B is the purified hPD-L1(ECD)-Fc protein, and C is the purified hPD-L1(ECD)-Fc protein after the Fc tag protein being removed by TEV enzyme, D is the purified PD-L1 Nb-Fc protein, and E is the biotinylated PD-1-Fc protein. All of the above proteins were expressed by HEK293F cells.

Upon extensive and intensive studies, the inventors have successfully obtained a class of anti-PD-L1 nanobodies after numerous screening. The experimental results show that the anti-PD-L1 nanobodies of the invention can effectively block the interaction between PD-L1 and PD-1. Surprisingly, the humanized anti-PD-L1 nanobodies of the invention can even more effectively block the binding between PD-L1 and PD-1. The BiaCore T200 analysis shows that the humanized anti-PD-L1 nanobodies have high affinity, superior stability and significant tumor inhibitory effect. Based on this discovery, the invention is completed.

In particular, the human PD-L1 protein as antigen was used to immunize a camel, thereby obtaining a gene library of nanobodies with high quality. The PD-L1 protein molecules were conjugated onto an ESLIA board and exhibited correct spatial structure of PD-L1 protein. The antigens in such configuration were used to screen the gene library of nanobodies by phage exhibition technology (phage exhibition of a gene library of camel heavy chain antibody) thereby obtaining genes of nanobodies with PD-L1 specificity. Then the genes were transferred into *E. coli* thereby obtaining the stains which can be effectively expressed in *E. coli* with high specificity.

As used herein, the terms "nanobodies of the invention", "anti-PD-L1 nanobodies of the invention", and "PD-L1 nanobodies of the present invention" are exchangeable and refer to nanobodies that specifically recognize and bind to PD-L1 (including human PD-L1). The more preferable nanobody is one comprising a VHH chain of amino acid sequence as set forth by SEQ ID NO.:8 or 14.

As used herein, the term "antibody" or "immunoglobulin" is a heterotetrameric glycosaminoglycan protein of about 150,000 Dalton with the same structural features, consisting of two identical light (L) chains and two identical heavy (H) chains. Each light chain is linked to the heavy chain through a covalent disulfide bond, and the number of disulfide bonds between the heavy chains of different immunoglobulin isoforms is different. Each heavy and light chain also has intra-chain disulfide bonds which are regular spaced. Each heavy chain has a variable region (VH) at one end followed by a plurality of constant regions. Each light chain has a variable region (VL) at one end and a constant region at the other end; the constant region of the light chain is opposite to the first constant region of the heavy chain, and the variable region of the light chain is opposite to the variable region of the heavy chain. Special amino acid residues form an interface between the variable regions of the light and heavy chains.

As used herein, the terms "single domain antibody (VHH)" and "nanobodies" have the same meaning referring to a variable region of a heavy chain of an antibody, and construct a single domain antibody (VHH) consisting of only one heavy chain variable region. It is the smallest antigen-binding fragment with complete function. Generally, the antibodies with a natural deficiency of the light chain and the heavy chain constant region 1 (CH1) are first obtained, the variable regions of the heavy chain of the antibody are therefore cloned to construct a single domain antibody (VHH) consisting of only one heavy chain variable region.

As used herein, the term "variable" refers that certain portions of the variable region in the nanobodies vary in sequences, which forms the binding and specificity of various specific antibodies to their particular antigen. However, variability is not uniformly distributed throughout the nanobody variable region. It is concentrated in three segments called complementarity-determining regions (CDRs) or hypervariable regions in the variable regions of the light and heavy chain. The more conserved part of the variable region is called the framework region (FR). The variable regions of the natural heavy and light chains each contain four FR regions, which are substantially in a β-folded configuration, joined by three CDRs which form a linking loop, and in some cases can form a partially β-folded structure. The CDRs in each chain are closely adjacent to the others by the FR regions and form an antigen-binding site of the nanobody with the CDRs of the other chain (see Kabat et al., NIH Publ. No. 91-3242, Volume I, pages 647-669. (1991)). The constant regions are not directly involved in the binding of the nanobody to the antigen, but they exhibit different effects or functions, for example, involve in antibody-dependent cytotoxicity of the antibodies.

As known by those skilled in the art, immunoconjugates and fusion expression products include: conjugates formed by binding drugs, toxins, cytokines, radionuclides, enzymes, and other diagnostic or therapeutic molecules to the nanobodies or fragments thereof of the present invention. The invention also includes a cell surface marker or an antigen that binds to said anti-PD-L1 protein nanobody or the fragment thereof.

As used herein, the term "heavy chain variable region" and "$V_H$" can be used interchangeably.

As used herein, the terms "variable region" and "complementary determining region (CDR)" can be used interchangeably.

In another preferred embodiment, the heavy chain variable region of said nanobody comprises 3 complementary determining regions: CDR1, CDR2, and CDR3.

In another preferred embodiment, the heavy chain of said nanobody comprises the above said heavy chain variable region and a heavy chain constant region.

According to the present invention, the terms "nanobody of the invention", "protein of the invention", and "polypeptide of the invention" are used interchangeably and all refer to a polypeptide, such as a protein or polypeptide having a heavy chain variable region, that specifically binds to PD-L1 protein. They may or may not contain a starting methionine.

The invention also provides other proteins or fusion expression products having the nanobodies of the invention. Specifically, the present invention includes any protein or protein conjugate and fusion expression product (i.e. immunoconjugate and fusion expression product) having a heavy chain containing a variable region, as long as the variable region are identical or at least 90% identical, preferably at least 95% identical to the heavy chain of the nanobody of the present invention.

In general, the antigen-binding properties of a nanobody can be described by three specific regions located in the variable region of the heavy chain, referred as variable regions (CDRs), and the segment is divided into four frame regions (FRs). The amino acid sequences of four FRs are relatively conservative and do not directly participate in binding reactions. These CDRs form a loop structure in which the β-sheets formed by the FRs therebetween are spatially close to each other, and the CDRs on the heavy chain and the CDRs on the corresponding light chain constitute the antigen-binding site of the nanobody. The amino acid sequences of the same type of nanobodies can be compared to determine which amino acids constitute the FR or CDR regions.

The variable regions of the heavy chains of the nanobodies of the invention become a particular interest because at least a part of them is involved in binding antigens. Thus, the present invention includes those molecules having a nanobody heavy chain variable region with a CDR, provided that their CDRs are 90% or more (preferably 95% or more, the most preferably 98% or more) identical to the CDRs identified herein.

The present invention includes not only intact nanobodies but also fragment(s) of immunologically active nanobody or fusion protein(s) formed from nanobodies with other sequences. Therefore, the present invention also includes fragments, derivatives and analogs of the nanobodies.

As used herein, the terms "fragment," "derivative," and "analog" refer to a polypeptide that substantially retains the same biological function or activity of a nanobody of the invention. Polypeptide fragments, derivatives or analogs of the invention may be (i) polypeptides having one or more conservative or non-conservative amino acid residues (preferably non-conservative amino acid residues) substituted. Such substituted amino acid residues may or may not be encoded by the genetic code; or (ii) a polypeptide having a substituent group in one or more amino acid residues; or (iii) a polypeptide formed by fusing a mature polypeptide and another compound (such as a compound that increases the half-life of the polypeptide, for example, polyethylene glycol); or (iv) a polypeptide formed by fusing an additional amino acid sequence to the polypeptide sequence (e.g., a leader or secretory sequence or a sequence used to purify this polypeptide or a proprotein sequence, or a fusion protein formed with a 6 His tag). According to the teachings herein, these fragments, derivatives, and analogs are within the scope of one of ordinary skill in the art.

The nanobody of the present invention refers to a polypeptide including the above CDR regions having PD-L1 protein binding activity. The term also encompasses variant forms of polypeptides comprising the above CDR regions that have the same function as the nanobodies of the invention. These variations include, but are not limited to, deletion insertions and/or substitutions of one or several (usually 1-50, preferably 1-30, more preferably 1-20, optimally 1-10) amino acids, and addition of one or several (generally less than 20, preferably less than 10, and more preferably less than 5) amino acids at C-terminus and/or N-terminus. For example, in the art, the substitution of amino acids with analogical or similar properties usually does not alter the function of the protein. For another example, addition of one or several amino acids at the C-terminus and/or N-terminus usually does not change the function of the protein. The term also includes active fragments and active derivatives of the nanobodies of the invention.

The variant forms of the polypeptide include: homologous sequences, conservative variants, allelic variants, natural mutants, induced mutants, proteins encoded by DNAs capable of hybridizing with DNA encoding the nanobody of the present invention under high or low stringent conditions, and polypeptides or proteins obtained using antiserum against the nanobodies of the invention.

The invention also provides other polypeptides, such as a fusion protein comprising nanobodies or fragments thereof. In addition to almost full-length polypeptides, the present invention also includes fragments of the nanobodies of the invention. Typically, the fragment has at least about 50 contiguous amino acids of the nanobody of the invention, preferably at least about 50 contiguous amino acids, more preferably at least about 80 contiguous amino acids, and most preferably at least about 100 contiguous amino acids.

In the present invention, "a conservative variant of a nanobody of the present invention" refers to the polypeptides in which there are up to 10, preferably up to 8, more preferably up to 5, and most preferably up to 3 amino acids substituted by amino acids having analogical or similar properties, compared to the amino acid sequence of the nanobody of the present invention. These conservative variant polypeptides are preferably produced according to the amino acid substitutions in Table 1.

TABLE 1

| Original residue | Representative substitution | Preferable substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |

TABLE 1-continued

| Original residue | Representative substitution | Preferable substitution |
|---|---|---|
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides a polynucleotide molecule encoding the above nanobody or fragment or fusion protein thereof. Polynucleotides of the invention may be in the form of DNA or RNA. DNA forms include cDNA, genomic DNA, or synthetic DNA. DNA can be single-stranded or double-stranded. DNA can be a coding strand or a non-coding strand.

Polynucleotides encoding the mature polypeptides of the invention include: coding sequences only encoding mature polypeptide; coding sequences for the mature polypeptide and various additional coding sequences; coding sequences (and optional additional coding sequences) and non-coding sequences for the mature polypeptide.

The term "polynucleotide encoding a polypeptide" may include a polynucleotide that encodes the polypeptide, and may also include a polynucleotide that includes additional coding and/or non-coding sequences.

The invention also relates to polynucleotides that hybridize to the sequences described above and that have at least 50%, preferably at least 70%, and more preferably at least 80% identity between the two sequences. The present invention specifically relates to polynucleotides that can be hybridized to the polynucleotides of the present invention under stringent conditions. In the present invention, "stringent conditions" refers to: (1) hybridization and elution at lower ionic strength and higher temperature, such as 0.2× SSC, 0.1% SDS, 60° C.; or (2) additional denaturants during hybridization, such as 50% (v/v) formamide, 0.1% fetal bovine serum/0.1% Ficoll, 42° C., etc.; or (3) hybridization occurs only under the identity between the two sequences at least over 90%, preferably over 95%. Also, polypeptides encoded by hybridizable polynucleotides have the same biological functions and activities as mature polypeptides.

The full-length nucleotide sequence of the nanobody of the present invention or a fragment thereof can generally be obtained by a PCR amplification method, a recombination method, or an artificial synthesis method. One possible method is to synthesize related sequences using synthetic methods, especially when the fragment length is short. In general, a long sequence of fragments can be obtained by first synthesizing a plurality of small fragments and then connecting them. In addition, the coding sequence of the heavy chain and the expression tag (eg, 6His) can be fused together to form a fusion protein.

Once the concerned sequences have been obtained, the concerned sequences can be obtained in large scale using recombinant methods. Usually, sequences can be obtained by cloning it into a vector, transferring it into cells, and then isolating the sequences from the proliferated host cells by conventional methods. Bio-molecules (nucleic acids, proteins, etc.) to which the present invention relates include bio-molecules that exist in isolated form.

At present, DNA sequences encoding the protein of the present invention (or a fragment thereof, or a derivative thereof) can be obtained completely by chemical synthesis. The DNA sequence then can be introduced into various existing DNA molecules (or e.g. vectors) and cells known in the art. In addition, mutations can also be introduced into the protein sequences of the invention by chemical synthesis.

The invention also relates to vectors comprising the above-mentioned suitable DNA sequences and suitable promoters or control sequences. These vectors can be used to transform an appropriate host cell so that it can express the protein.

The host cell can be a prokaryotic cell, such as a bacterial cell; or a lower eukaryotic cell, such as a yeast cell; or a higher eukaryotic cell, such as a mammalian cell. Representative examples are: *Escherichia coli, Streptomyces*, bacterial cells such as *Salmonella typhimurium*, fungal cells such as yeast, insect cells of *Drosophila* S2 or Sf9, animal cells of CHO, COS7, 293 cells, and the like.

The transformation of the host cell with the recombinant DNA can be performed using conventional techniques well known to those skilled in the art. When the host is a prokaryotic organism such as *E. coli*, competent cells capable of absorbing DNA can be harvested after the exponential growth phase and treated with the $CaCl_2$ method. The procedures used are well known in the art. Another method is to use $MgCl_2$. If necessary, conversion can also be performed by electroporation. When the host is eukaryotic, the following DNA transfection methods can be used: calcium phosphate coprecipitation, conventional mechanical methods such as microinjection, electroporation, liposome packaging, and the like.

The obtained transformants can be cultured in a conventional manner to express the polypeptide encoded by the gene of the present invention. Depending on the host cells used, the medium used in the culture may be selected from various conventional media. The culture is performed under conditions suitable for the host cells growth. After the host cells are grown to an appropriate cell density, the selected promoter is induced by a suitable method (such as temperature shift or chemical induction) and the cells are incubated for a further period of time.

The recombinant polypeptide in the above method may be expressed intracellularly, or on the cell membrane, or secreted extracellularly. If necessary, the recombinant protein can be isolated and purified by various separation methods by utilizing its physical, chemical and other characteristics. These methods are well-known to those skilled in the art. Examples of these methods include, but are not limited to: conventional renaturation treatment, treatment with a protein precipitation agent (salting out method), centrifugation, osmotic disruption, super treatment, ultra-centrifugation, molecular sieve chromatography (gel filtration), adsorption layer analysis, ion exchange chromatography, high performance liquid chromatography (HPLC), and various other liquid chromatography techniques and the combinations thereof.

The nanobodies of the invention may be used alone or in combination or conjugated with a detectable marker (for diagnostic purposes), a therapeutic agent, a PK (protein kinase) modification moiety, or a combination thereof.

Detectable markers for diagnostic purposes include, but are not limited to: fluorescent or luminescent markers, radioactive markers, MRI (magnetic resonance imaging) or CT (computed tomography) contrast agents, or enzymes capable of producing detectable products.

Therapeutic agents that can be binded or conjugated to the nanobodies of the present invention include, but are not limited to: 1. Radionuclides; 2. Biological poisons; 3. Cytokines such as IL-2, etc.; 4. Gold nanoparticles/nanorods; 5. Viruses Particles; 6. Liposome; 7. Nano magnetic particles; 8. Prodrug activating enzymes (for example, DT-diaphorase (DTD) or biphenyl hydrolase-like protein (BPHL)); 10. Chemotherapeutic agents (for example, cisplatin) or any form of nanoparticles, etc.

Pharmaceutical Composition

The invention also provides a composition. Preferably, said composition is a pharmaceutical composition comprising the above nanobody or active fragment or fusion protein thereof, and a pharmaceutically acceptable carrier. In general, these materials can be formulated in non-toxic, inert, and pharmaceutically acceptable aqueous carrier media wherein the pH is generally about 5-8, preferably about 6-8, although the pH can be varied with the nature of the formulation material and the condition to be treated. The formulated pharmaceutical compositions can be administered by conventional routes including, but not limited to, intratumoral, intraperitoneal, intravenous, or topical administration.

The pharmaceutical composition of the present invention can be directly used to bind PD-L1 protein molecules and thus can be used to treat tumors. In addition, other therapeutic agents can also be used at the same time.

The pharmaceutical composition of the present invention contains a safe and effective amount (for example, 0.001-99 wt %, preferably 0.01-90 wt %, and more preferably 0.1-80 wt %) of the above-mentioned nanobodies of the present invention (or their conjugates) and pharmaceutically acceptable carriers or excipients. Such carriers include, but are not limited to: saline, buffer, dextrose, water, glycerol, ethanol, and the combinations thereof. The drug formulation should be suitable for the mode of administration. The pharmaceutical composition of the present invention may be prepared in the form of an injection, for example, by a conventional method using physiological saline or an aqueous solution containing glucose and other adjuvant. Pharmaceutical compositions such as injections and solutions are preferably made under aseptic conditions. The amount of active ingredient administered is a therapeutically effective amount, for example, about 10 micrograms/kilogram body weight to about 50 milligrams/kilogram body weight per day. In addition, the polypeptides of the invention can also be used with other therapeutic agents.

When a pharmaceutical composition is used, a safe and effective amount of the immune-conjugate is administered to the mammal, wherein the safe and effective amount is usually at least about 10 micrograms/kilogram body weight, and in most cases, no more than about 50 mg/kilogram body weight, preferably the dose is about 10 micrograms/kilogram body weight to about 10 milligrams/kilogram body weight. Of course, factors such as the route of administration and the patient's health status should be considered to define the specific doses, all of which are within the skills of skilled physicians.

Nanobodies with Markers

In a preferred embodiment of the invention, the nanobodies carry detectable markers. More preferably, the marker is selected from the group consisting of isotopes, colloidal gold markers, colored markers, and fluorescent markers.

Colloidal gold markers can be performed using methods known to those skilled in the art. In a preferred embodiment of the invention, the anti-PD-L1 nanobodies are marked with colloidal gold to obtain colloidal gold-markered nanobodies.

The anti-PD-L1 nanobodies of the present invention have very good specificity and high potency.

Detection Method

The invention also relates to a method of detecting PD-L1 protein. The method steps are basically as follows: obtaining a sample of cells and/or tissue; dissolving the sample in a medium; and detecting the level of PD-L1 protein in the dissolved sample.

According to the detection method of the present invention, the sample used is not particularly limited, and a representative example is a sample containing cells which is present in a cell preservation solution.

Kits

The present invention also provides a kit containing a nanobody (or a fragment thereof) or a detection board of the present invention. In a preferred embodiment of the present invention, the kit further includes a container, an instruction, a buffer, and the like.

The present invention also provides a detection kit for detecting the level of PD-L1, and said kit comprises nanobodies that recognize PD-L1 protein, a lysis medium for dissolving a sample, a general reagent and a buffer needed for the detection, such as various buffer, detection markers, detection substrates, etc. The test kit can be an in vitro diagnostic device.

Application

As described above, the nanobodies of the present invention have extensive biological application value and clinical application value. Said applications involve various fields such as diagnosis and treatment of diseases related to PD-L1, basic medical research, and biological research. One preferred application is for clinical diagnosis and targeted treatment of PD-L1.

The Main Advantages of the Present Invention Include:

(a) the nanobodies of the invention are anti-PD-L1 proteins with high specificity for humans and a correct spatial structure;

(b) the nanobodies of the invention have a strong affinity; and (c) the nanobodies of the invention are simple to produce.

The present invention is further described in combination with specific embodiments. It should be understood that these examples are only for illustrating the present invention and are not intended to limit the scope of the present invention.

The experimental methods that do not specify the specific conditions in the following examples are generally performed according to conventional conditions such as those described in Sambrook et al., Molecular Cloning: A Laboratory Manual (New York: Cold Spring Harbor Laboratory Press, 1989), or according to the conditions recommended by the manufacturer. Unless otherwise indicated, percentages and parts are percentages by weight and parts by weight.

Example 1: Expression and Purification of Human PD-L1 Protein (1) The human PD-L1 nucleotide sequence was integrated into pCDNA3.1(−) vector (commercially available from Invitrogen) and the sequence of the extracellular domain was sub-cloned into pFUSE-IgG1 vector (commercially available from Invitrogen), wherein a TEV cleavage site was introduced at C-terminal of hPD-L1(ECD) to facilitate the preparation of a hPD-L1(ECD) with Fc-tag.

(2) An Omega plasmid maxi kit was used to extract the constructed pFMSE-IgG1-hPD-L1(ECD) plasmid.

(3) HEK293F cells were cultured to an OD of $2.0 \times 10^6$ cells/mL.

(4) The plasmid and the transfection agent PEI were mixed (1:3) well and placed for 20 min, and then the product was added into HEK293F cells culture for further incubation in a shaker under 6% $CO_2$ at 37° C. for 5-6 days.

(5) The supernatant of the cells was collected and subjected to binding with Protein A beads at R.T. for 1 hour.

(6) After the beads were washed by PBS (pH 7.0), 0.1 M of Glycine (pH3.0) was used to elute the proteins.

(7) The eluted proteins were ultrafiltrated into PBS and sampled for an SDS-PAGE test after yield measurement (the test results are shown in FIG. 1B). The rest of the proteins were stored in a fridge at −80° C.

(8) The expressed hPD-L1(ECD)-Fc protein was cleavaged by using 0.1 mg TEV enzyme per 1 mg hPD-L1(ECD)-Fc protein at 4° C. for 16 hours. The protein solution was loaded onto a Ni column and a Protein A column subsequentially and the flow-through was collected and sampled to an SDS-PAGE test (the test results are shown in FIG. 1C).

Example 2: The Construction of PD-L1 Nanobody Library (1) 1 mg of hPD-L1 (ECD)-Fc antigen was mixed with Freund's adjuvant in equal volumes to immunize a Xinjiang bactrian camel once a week for a total of 7 times to stimulate B cells to express antigen-specific nanobodies;

(2) After the 7 immunizations were completed, 100 mL of camel peripheral blood lymphocytes were sampled and total RNA was extracted.

Figure 2:
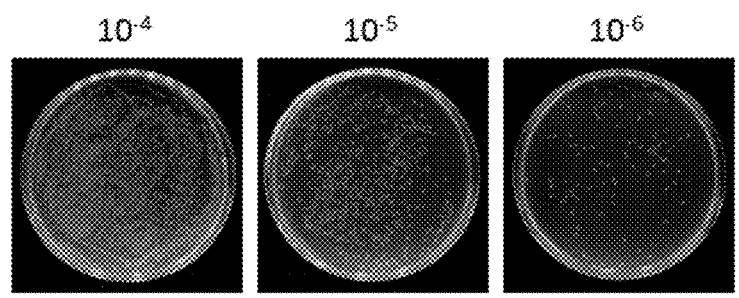
FIG. 2 shows the detection result for the library capacity of the constructed library. The constructed library was coated onto a plate after being serially diluted. The figure shows ⅕ of the clones with gradient dilution of $10^4$ fold, $10^5$ fold, and $10^6$ fold, and the number of clones was counted to determine the size of the library.

(3) cDNA was synthesized and VHH was amplified using nested PCR;

(4) 20 μg pMECS phage display vector (purchased from Biovector) and 10 μg VHH were digested with restriction endonucleases PstI and NotI and the two fragments were ligated together;

(5) The ligated product was electronically transfected into competent TG1 cells, and the PD-L1 nanobody library was constructed and the capacity thereof was determined. The capacity was $1.3 \times 10^9$ CFM (the results are shown in FIG. 2).

Figure 3:
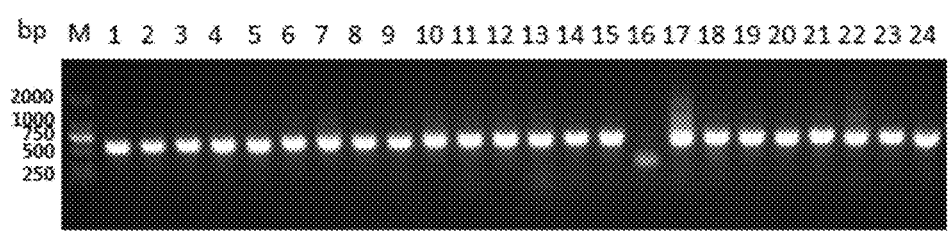
FIG. 3 is a detection result for the insertion rate of the constructed nanobody library. The DNA bands in the gel pores from left to right respectively correspond to DNA molecule marker for the first lane, and PCR products of detected insertion fragment for the other lanes. The PCR product lane is about 500 bp. The insertion rate as detected is up to 95.8%.

At the same time, 24 clones were picked randomly for PCR detection of colony. The results showed that the insertion rate of the constructed library was 100%. FIG. 3 shows the PCR results of colony.

Example 3: Screening and Verification of PD-L1 Nanobodies

Screening of Nanobodies (1) 10 μg hPD-L1 (ECD) antigens dissolved in 100 mM $NaHCO_3$ (pH 8.2) was coupled to the NUNC ELISA board and left overnight at 4° C.;

(2) 100 μL of 0.1% BSA was added on the next day and blocked at room temperature for 2 h.

Figure 4:
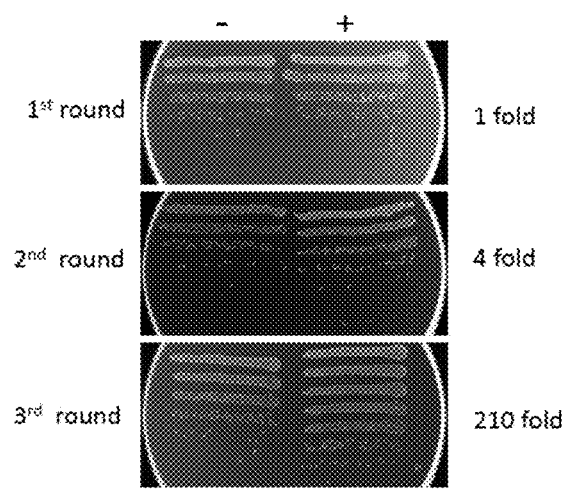
FIG. 4 shows the screening and enrichment process of PD-L1 nanobodies. There is no enrichment after the first round of panning. It is 4 times enriched after the second round of panning and 210 times enriched after the third round of panning.

(3) After 2 h, 100 μL of phages ($2 \times 10^{11}$ CFM of phage display gene library with nanobodies of immunized camel) was added and reacted at room temperature for 1 h;

(4) 0.05% PBS+Tween-20 were used for washing for 5 times to wash away non-specific phages; (5) The phages specifically binded to PD-L1 were dissociated by 100 mM triethanolamine, and E. coli TG1 cells in logarithmic phase were infected and incubated at 37° C. for 1 h. The phages were generated and purified for the next round of screening. The screening process was repeated for 3 rounds. The enrichment results are shown in FIG. 4.

Screening specific single positive clones by using phage-based enzyme-linked immunosorbent assay (ELISA):

(1) From the cell culture dishes containing bacteriophages obtained by above 2-3 rounds of screening, 96 single colonies were picked and inoculated in TB medium containing 100 μg/mL ampicillin (2.3 liter KH$_2$PO$_4$ in 1 liter TB medium. 12.52 g K$_2$HPO$_4$, 12 g peptone, 24 g yeast extract, 4 mL glycerol). After the cells grew to logarithmic phase, IPTG was added to a final concentration of 1 mM and cultured overnight at 28° C.

(2) Crude nanobodies were obtained by osmotic method, and the nanobodies were transferred to an antigen-coated ELISA board and allowed to place at room temperature for 1 hour.

(3) Unbound nanobodies were washed away with PBST and anti-mouse anti-HA nanobodies (purchased from Beijing Kangwei Century Biotechnology Co., Ltd.). The product was placed at room temperature for 1 hour.

(4) Unbound nanobodies ware washed away with PBST, and goat anti-mouse alkaline phosphatase-labeled nanobodies were added. The product was placed at room temperature for 1 hour.

(5) Unbound nanobodies were washed with PBST, and alkaline phosphatase staining solution was added. The absorbance was read at 405 nm on an ELISA instrument.

(6) When OD value of the sample well was over 3 times of the OD value of the control well (Ratio+/−>3), it is confirmed as a positive clone well.

(7) The bacteria in the positive clone wells were shaken in an LB liquid containing 100 μg/mL for plasmid extraction and sequencing.

Example 4: Expression of Nanobodies in *E. coli* Host and Purification (1) The plasmids obtained from the previously sequenced clones were electro-transformed into *E. coli* WK6 and then coated onto LA+Glucose (a culture plate containing ampicillin and glucose) for incubation overnight at 37° C.

(2) A single colony was picked, inoculated into 5 mL LB culture medium which contains ampicillin, and cultured in a shaker overnight at 37° C.;

(3) 1 mL overnight-cultured strains were inoculated into 330 mL TB medium and culture in a shaker at 37° C. to an OD value of 0.6-1. IPTG was added and the product was cultured in a shaker at 28° C. overnight.

(4) The product was subjected to centrifugation and the strains were collected.

(5) Using the osmosis method to obtain the crude nanobody extract.

Figure 5:
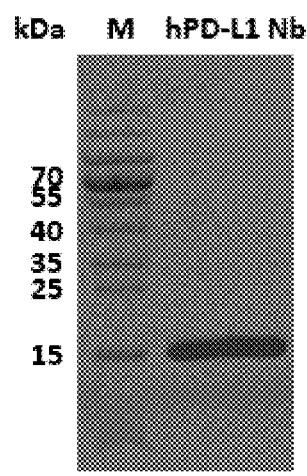
FIG. 5 is the illustration of purified PD-L1 nanobodies (corresponding to the nanobody of the amino acid of SEQ ID NO.: 8) expressed by *E. coli*. It is an SDS-PAGE electrophoretogram of PD-L1 nanobody upon the resin gel affinity chromatography purification by nickel column. The results turned out that the purity of PD-L1 reaches over 90% after the purification.

(6) Nanobodies with a purity of over 90% were prepared by Ni ion column affinity chromatography. The purification results are shown in FIG. 5.

Example 5: The Blocking Effects of Nanobodies Tested by Flow Cytometry (1) hPD-1-Fc-Biotin proteins were prepared (The preparation method for hPD-1-Fc was identical with Example 1. The SDS-PAGE test results are shown in FIG. 1E). The biotinylation of the proteins were conducted according to the biotin reagent instructions.

(2) 1×10$^6$ of HEK293F cells transiently expressing human PD-L1 full-length protein were taken from each sample and resuspended in 0.5% BSA-PBS buffer, and 10 μg of the above-mentioned purified PD-L1 nanobodies were added. hIgG1 was set as a negative control and PBS was for blank group. 5 μg of hPD-1-Fc-biotins were added into all the samples for each and subjected to incubation at 4° C. for 20 min.

Figure 6:
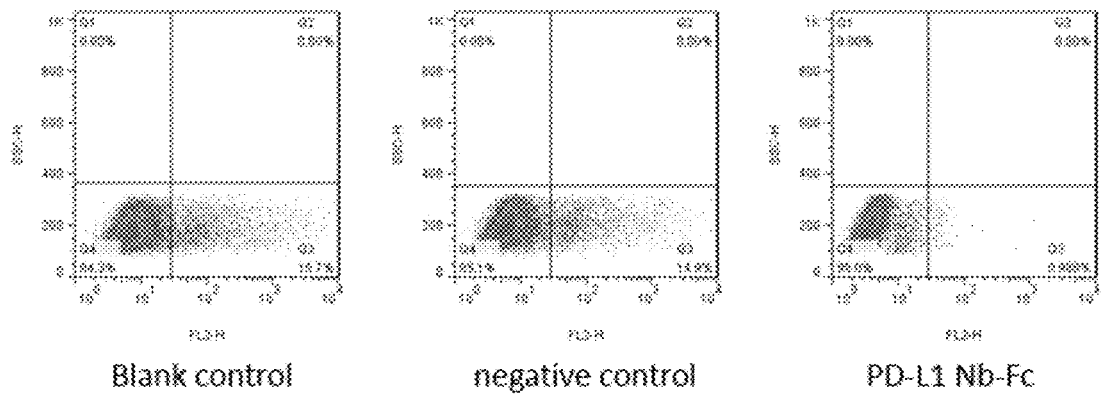
FIG. 6 shows the blocking effects of PD-L1 nanobodies tested by FACS. It is conducted by the co-reaction of HEK293F cells instantly expressing human full-length PD-L1 protein, various groups of nanobodies and biotinylated hPD-1-Fc protein.

(3) The cells were washed twice with PBS, and SA-PE (purchased from eBioscience) was added. The product was incubated at 4° C. for 20 minutes. A flow cytometry (BD FACS Calibur) was used for determine the cells after they were washed twice with PBS. The determination results were shown in FIG. 6.

Humanization of PD-L1 nanobodies (1) Firstly, the PD-L1 nanobody sequence of SEQ ID NO.: 8 was used as a template to search for homologous structures in the structural database. A total of 1306 structures were found, wherein 34 structures were taken (E value=0.0, and sequence identity ≥70%);

(2) These 34 structures were subjected to structural comparison. Based on the resolution of the crystal structure and the constructed evolutionary tree, 9 proteins including 3dwt were finally selected for multi-template homology modeling based on the PD-L1 nanobody sequence of SEQ ID NO.: 8. Finally, 10 structures were obtained. The structures with lowest molpdf were selected according to the ranking of the scoring function from top to bottom and then left for the further process.

(3) For those best structures obtained from modeling, the solvent accessibility of the residues calculated by ProtSA server (i.e. the ratio of the solvent contactable surface of the residues between folding and folding state) was used as a cut-off value. The residues with a value over 40% were taken as the residues exposed to the solvent.

(4) An alignment was conducted between the best structures obtained from modeling and DP-47 sequence and the corresponding residues exposed to the solvent were substituted. A humanized PD-L1 nanobody of the amino acid sequence as set forth by SEQ ID NO.: 14 was ultimately determined. The sequences of the nanobodies before and after humanization were shown in Table 2:

TABLE 2

| nanobody domain | SEQ ID NO.: | |
|---|---|---|
| | Before humanization | After humanization |
| FR1 | 1 | 10 |
| CDR1 | 5 | 5 |
| FR2 | 2 | 11 |
| CDR2 | 6 | 6 |
| FR3 | 3 | 12 |
| CDR3 | 7 | 7 |
| FR4 | 4 | 13 |
| Full amino acid sequence | 8 | 14 |
| Full nucleotide sequence | 9 | 15 |

The comparison of the identity between the nanobody framework region and the DP-47 framework region before and after humanization is shown in Table 3 below:

TABLE 3

| nanobody domain | The identity with DP-47 | |
|---|---|---|
| | Before humanization | After humanization |
| FR1 | 80% | 92% |
| FR2 | 66.67% | 80% |
| FR3 | 76.32% | 89.47% |
| FR4 | 90.91% | 100% |

Example 6: The Activity of Anti-PD-L1 Nanobodies Determined by Using MOA Method In this experiment, two commercially available anti-PD-L1 nanobodies (Atezolizumab, A T E and Durvalumab, DUR) was taken as positive control nanobodies, and the cell lines (Promega) were detected using MOA. The activation of the NFAT signal was reflected by determining the fluorescent reporter gene, thereby detecting the inhibitory effects of the nanobodies (sequence shown in Example 5) on PD-1/PD-L1 binding. The steps were shown as follows:

(1) CHOK1-PDL1 cells were plated one day before the activity assay: CHOK1-PDL1 was passaged 1-2 days before. The culture supernatant was discarded and the resultant was washed with PBS. Appropriate amounts of trypsin were added to digest at 37° C./5% $CO_2$ for 3-5 min. Culture medium at 4 times the volume of trypsin was added, and the cells were transferred to a 50 ml centrifuge tube and subjected to cells counting. Cells with required volume were centrifuged for 10 min at 230 g. The medium was added and the cells were resuspended to $4\times10^5$ cells/mL. The cells were added to a white 96-well cell culture plate at 100 µl/well. PBS was added to the side wells at 200 µl/well. Cells were incubated in a 37° C./5% $CO_2$ incubator overnight.

(2) Treatment of Jurkat-PD1 cells: Cells were passaged two days prior to the activity assay. After counting, cells of required volume were centrifuged for 5 min at 170 g. The cells were resuspended in assay buffer to $1.25\times10^6$ cells/ml.

(3) The samples and Jurkat-PD1 cells were added to the assay plate: the supernatant of CHOK1-PDL1 cells (95 µl/well) was discarded. 40 µl of sample (purify nanobodies obtained from hybridoma supernatant or serially diluted hybridoma supernatant) positive controls, and negative controls were added. 40 µl of Jurkat-PD1 cells were added and the resultant was incubated in a 37° C./5% $CO_2$ incubator for 6 hours.

(4) Assay: The Bio-Glo™ buffer was thawed in advance, and Bio-Glo™ substrate was added and mixed well. After 6 hours, Bio-Glo™ Reagent was added at 80 µl/well and placed at room temperature for 5-10 minutes for reading.

Figure 11:
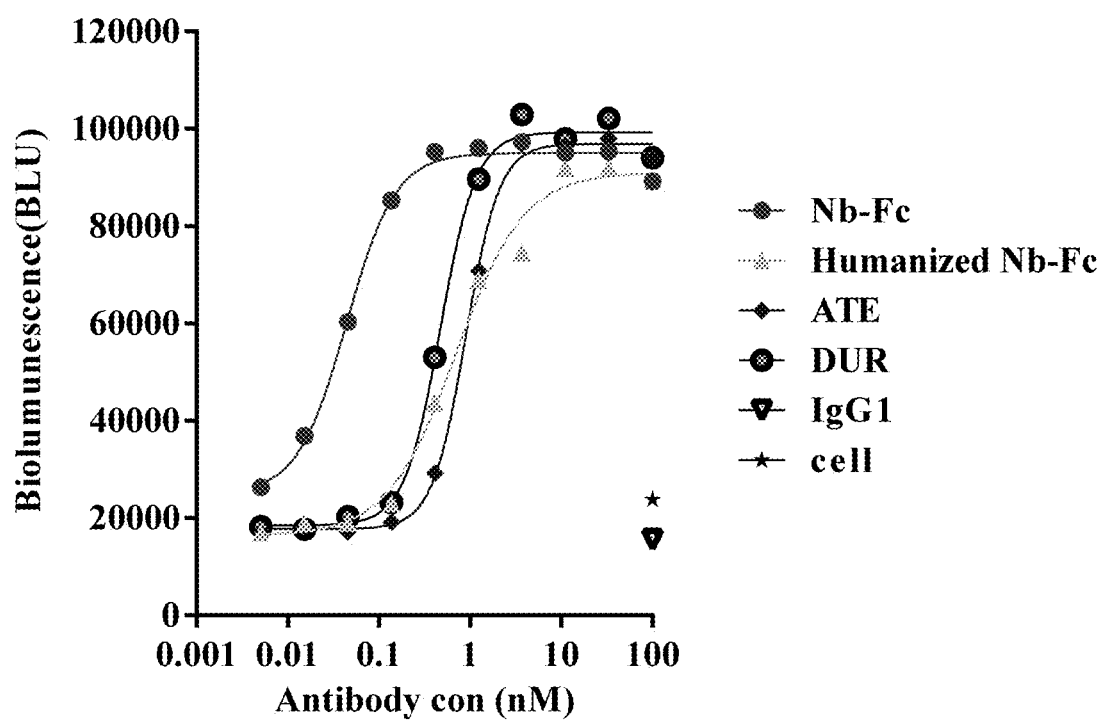
FIG. 11 shows the inhibition effects of nanobodies on the interaction between PD-1 and PD-L1 by MOA method, wherein the nanobodies before humanization have stronger activity than that of the antibodies in the positive control group while the nanobodies after humanization have comparable activity to that of the antibodies in the positive control group.

The results of the experiments are shown in Table 4 and FIG. 11. Under various concentrations, the nanobodies of the present invention before humanization were generally more active than the positive control, and the activity of the nanobodies of the invention after humanization was comparable to that of the positive control. Therefore, both Nb-Fc and humanized Nb-Fc nanobodies can effectively block PD1/PD-L1 interactions.

TABLE 4

| Concentration (nm) | Nb-Fc | humanized Nb-Fc | ATE | DUR | IgG1 | Cell |
|---|---|---|---|---|---|---|
| 100.000 | 89222 | 89341 | 94006 | 94061 | 15659.5 | 23860 |
| 33.333 | 95361 | 92060 | 97992 | 102218 | | |
| 11.111 | 95122 | 92012 | 96453 | 97936 | | |
| 3.704 | 97307 | 74598 | 96932 | 102944 | | |
| 1.235 | 96119 | 68937 | 70803 | 89708 | | |
| 0.412 | 95249 | 43734 | 29286 | 53071 | | |
| 0.137 | 85291 | 23035 | 19240 | 23210 | | |
| 0.046 | 60302 | 19080 | 17246 | 20308 | | |
| 0.015 | 36885 | 19016 | 18355 | 17757 | | |
| 0.005 | 26336 | 17079 | 16927 | 18243 | | |

Example 7: Expression of Humanized PD-L1 Nanobodies in Eukaryocyte HEK293 and Purification (1) The PD-L1 Nb sequences before and after humanization were synthesized to the pFUSE-IgG1 vector (purchased from Invivogen), and the pFUSE-IgG1-Nb plasmid (humanized) was extracted using Omega plasmid maxi kit.

(2) HEK293F cells were cultured to an OD of $2.0\times10^6$ cells/mL;

(3) The plasmid and the transfection reagent PEI (1:3) were mixed and allowed to stand for 20 min, then added to HEK293F cells, and cultured in a 6% $CO_2$ shaker at 37° C. for 5-6 days;

(4) The cell supernatants were collected and subjected to the binding with Protein A beads at room temperature for 1 hour;

(5) After washing the beads with phosphate buffer (pH 7.0), the proteins were eluted with 0.1 M Glycine pH 3.0;

(6) The eluted proteins were ultrafiltrated into PBS, and the yield was measured. Then the samples were analyzed by SDS-PAGE (the results are shown in FIG. 1D and FIG. 7). The remaining proteins were stored in a refrigerator at −80° C. It can be seen from FIG. 7 that the purity of humanized nanobodies reaches more than 90%.

Example 8: Blocking Effects of the Humanized PD-L1 Nanobodies Determined by Flow Cytometry The method is identical with Example 5:

(1) $2\times10^5$ human lung cancer cell lines (EBC-1) naturally expressing PD-L1 in each sample were resuspended in 0.5% BSA-PBS buffer and 10 µg of purified humanized PD-L1 nanobodies were added. hIgG1 was set as the negative control group and PBS as the blank group. 5 µg hPD-1-Fc-biotin was added into each sample, and the products were incubated at 4° C. for 20 min;

(2) The cells were washed with PBS twice, and SA-PE from eBioscience was added. The resultants were incubated for 20 minutes at 4° C., and the cells were washed with PBS twice and loaded for tests. The results are shown in FIG. 8: it could be seen from the blank and the negative control, the binding rate of PD-1-Fc-biotin to EBC-1 cells was above 90%. While after the addition of PD-L1 nanobodies and humanized nanobodies, the binding rate of PD-1-Fc-biotin to EBC-1 cells was less than 10%. This indicates that the added nanobodies can significantly block the interaction of PD-1 with PD-L1.

Example 9: Determination on the Affinity of the Nanobodies

BiaCore T200 was used for detection. (1) Immobilization: The immobile phase antigens were immobilized on the surface of a CM-5 sensor chip using a carboxy-amino reaction;

(2) Binding: The nanobodies were diluted with HBS buffer to an appropriate concentration (five concentration gradients) to observe the antigen-nanobody binding process;

(3) Chip regeneration: When performing the next nanobody measurement, 10 mM Glycine was used for regeneration.

(4) Analysis of the experimental results. The results of the assay are shown in FIG. 9. The affinity of nanobodies before humanization was $2.34\times10^{-9}$ M, and the affinity of humanized nanobodies was $2.26 \times 10^{-9}$ M. Humanization does not change the affinity of the nanobody.

Example 10: The Specificity of Purified Nanobodies by ELISA (1) The nanobodies before and after humanization were biotinylated by conventional methods;

(2) The antigen proteins PD-L1 (human), PD-L1 (rat), PD-L1 (monkey), PD-L2 (human), B7H4 (human), B7H3 (human) were coated: 0.5 µg per well (5 µg/mL, 100 µL), IgG1 was coated as a control, left overnight at 4° C.;

(3) The products were washed by PBST 3 times, and 200 µL, 1% BSA was added to block in RT for 2 hours;

(4) Each biotinylated nanobodies were diluted to 10 µg/mL, and 100 µL of each was incubated in each well and allowed to react at RT for 1 hour.

(5) The unbound nanobodies were washed with PBST, 100 µL of streptavidin-HRP (1:1000 dilution) was added, and the resultant was let stand for 1 hour at room temperature.

Figure 10:
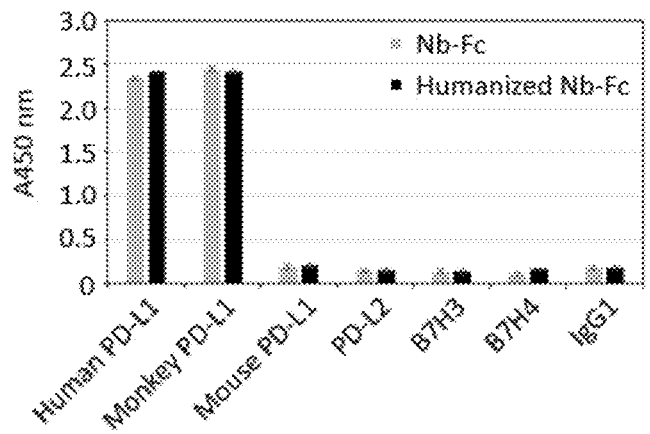
FIG. 10 shows the specificity results of PD-L1 nanobodies tested by ELISA. It could be seen that PD-L1 nanobodies before and after humanization only interact with human and Cercopithecidae PD-L1 instead of Muroidea or other member of PD-L1 family. Both of the two nanobody strains have good specificity.

(6) The color development solution was added and the absorbance at the wavelength of 450 nm was read on ELISA. The specificity of the nanobodies was determined based on the absorbance values. The results are shown in FIG. 10. Both of the nanobodies before and after humanization interacted with human and monkey-derived PD-L1 but not with the mouse-derived PD-L1. The two nanobodies had good species specificity. Neither of the nanobodies before or after humanization interacted with PD-L1 family members and had good family specificity.

Example 11: Tests on Mixed Lymphocytes

In this experiment, nanobodies were incubated with mature DC cells and CD4+ T cells derived from different donors and cultured in vitro. The relative expression levels of IL2 and IFN-γ in the system were detected to reflect the activation of T cells by different nanobodies. The steps are as follows:

(1) PBMC isolation: 50 ml fresh blood from the donors was taken, and 2.5 times of PBS was added. The product was gently added into FiColl (Thermo) (12.5 ml, 4 tubes), centrifuged at 400 g for 30 min, and stopped at 0 deceleration. The middle white band was aspirated into PBS (Gibco) and washed twice with PBS.

(2) DC cell isolation: The isolated PBMC cells were taken and 5 ml of T cell culture medium was added. The cells were subject to adherent culture at 37° C. under 6% $CO_2$ for 2 hrs. The suspending cells were taken to separate CD4+ cells. 3 ml of DC was added to the remaining cells. After 2 days of culture, 3 ml of DC medium was added for further culture to the fifth day. Then, rTNFa (R&D Systems) (1000 U/ml), IL-1b (R&D Systems) (5 ng/ml), IL-6 (R&D Systems) (10 ng/ml) and 1 µM PGE2 (Tocris) were cultured for 2 days as the DC cells for mixed lymphocyte reaction (MLR).

(3) Isolation of CD4+ cells: PBMCs were incubated for 2 hr and the suspended cells were drawn into 15 ml centrifuge tubes, centrifuged at 200 g for 10 min, resuspended in 500 µl of serum, 100 µl of AB serum, and 100 µl of purified nanobodies, incubated for 20 min at 4° C., and washed once with the separation solution. 500 µl of Bead Buffer was added for incubation for 15 min. The Bead was removed by magnetic field, washed once with T cell culture medium, resuspended with 8 ml culture medium, and incubated at 37° C. under 6% $CO_2$. (The procedures were conducted according to the instruction of 'Human CD4+ T Cell Enrichment Kit' (19052, Stemcell)).

(4) MLR experiment: The matured DC cells were mixed with CD4+ cells at a volume of 200 µl per well, 10,000 DC cells, and 100,000 CD4+ cells. nanobodies were added, DCs, T cells, and MLR were used as negative controls, and DC+T cells+anti-CD3/CD28 magnet beads were used as the positive control. The beads were subjected to mixed culture for 5 days, and a cisbio kit (Human IL2 Kit 1000 Test, Human IFN gamma 1000 test) was used to detect IL2 and IFN-gamma concentration.

Figure 12:
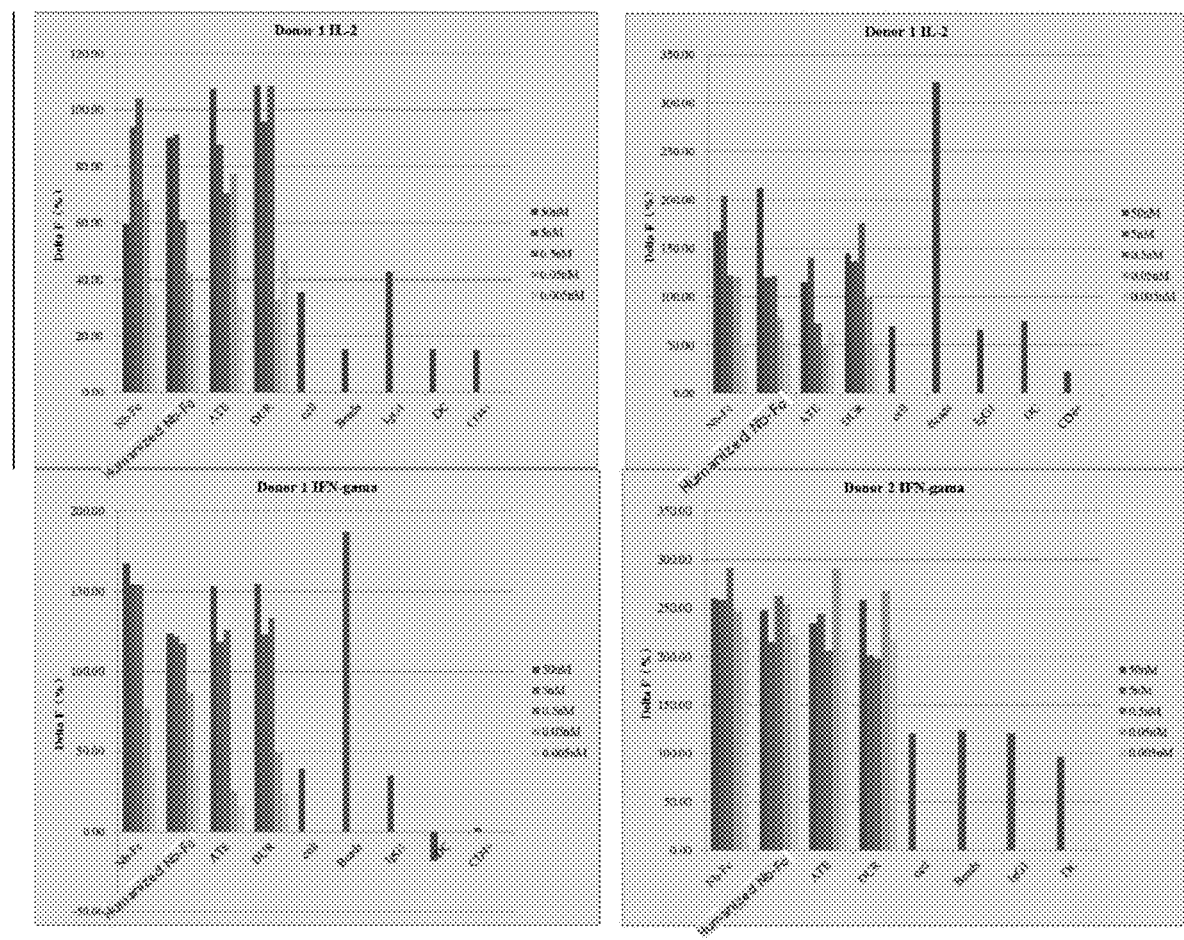
FIG. 12 shows the nanobodies and the humanized nanobodies can effectively activate T cells and have comparable effect of activation to that of the antibodies in the positive control group.

The experimental results are shown in FIG. 12. The nanobodies of the present invention (sequence shown in Example 5) stimulated the donor to produce more cytokines than the positive control. After humanization, the produced cytokines were comparable to the positive control. Therefore, both of the nanobodies of the present invention and the humanized nanobodies can effectively activate T cells, and the activation effect is similar to that of the antibody of positive control group.

Example 12 the Study on Tumor-Inhibiting Activities of Anti-PD-L1 Nanobodies

Figure 13:
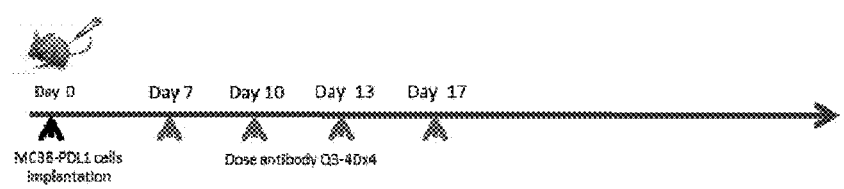
FIG. 13 shows the administration manner of the nanobodies of the invention in the study on tumor inhibition activity.

In this study, human PD-L1 expressing MC38 cells (MC38-PDL1) (Nanjing Galaxy) were used to determine the anti-tumor effects of humanized Nb-Fc in PD-L1 transgenic mice. Firstly, MC38-PDL1 tumor-bearing mice model was established by subcutaneous inoculation. After tumor formation, different nanobodies (sequences are shown in Example 5) and different doses of treatment were administered, and the tumor volumes and body weight changes in each group of mice were monitored during administration. Dosing frequency was 2 times/week, monitoring frequency was 2 times/week, and continuous monitoring last for 5 weeks. The dosage and methods were shown in Table 5 and FIG. 13.

TABLE 5

| Group | Testing subjects | dosage | Administration volume | concentration | Administration route |
|---|---|---|---|---|---|
| h-IgG | IgG control | 20 mg/kg | 10 ml/kg | 2.0 mg/ml | Intraperitoneal injection |
| humanized Nb-Fc | humanized Nb-Fc | 10 mg/kg | 10 ml/kg | 1.0 mg/ml | Intraperitoneal injection |

The steps are shown as follows:

1) The preparation of MC38/PD-L1 cell suspension: MC38 cells were dispensed with PBS (1×) to a cell density of 1×10$^7$ cells/ml to prepare the MC38 cell suspension;

2) Inoculation: 25 C57Bl/6 background PD-L1 mice were shaved at the right side of the back, and MC38/PD-L1 cells were subcutaneously injected with 1×10$^6$ cells/0.1 ml/body. After 6 days of tumor cell inoculation, the tumor volumes of each mouse were examined, and 25 mice with a tumor volume ranging from 87.4 mm$^3$ to 228.4 mm$^3$ were selected and grouped by average tumor volume.

3) Dosing: See FIG. 13.

4) Test: The weight before and after each administration and the body weight and tumor volumes were measured. Weights were measured using an electronic balance, 2 times per week.

5) Measurement of the tumor volumes: The maximum length (L) and the maximum width (W) of the tumors were measured using a vernier caliper. The tumor volumes were calculated according to the following formula: V=L×W$^2$/2.

Figure 14:
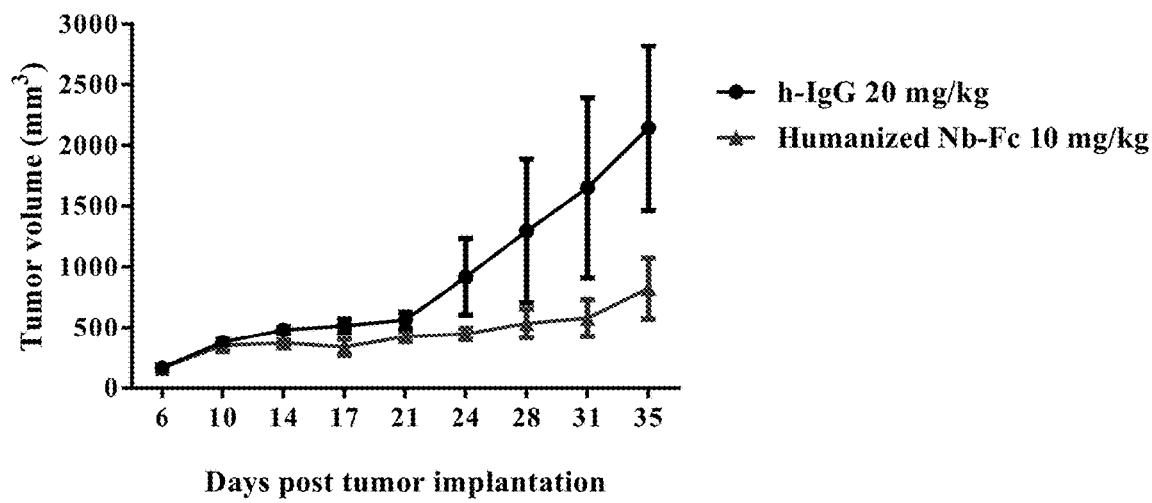
FIG. 14 shows the tumor volume is better inhibited than that in the control group in the mice inoculated with humanized Nb-Fc, and no significant increase (in tumor size) is observed, suggesting that the humanized Nb-Fc has significant tumor inhibiting effect.

The results of the experiments are shown in FIG. 14. The mice vaccinated with humanized Nb-Fc had a very good control of tumor volumes comparing to the control group and showed no significant increase, indicating humanized Nb-Fc has a significant tumor inhibiting effect.

Example 13. The Solubility of the Nanobodies Detected by PEG Precipitation Method In this experiment, the solubility of the nanobodies was reflected by PEG precipitation method through detecting the dissolution of alternative nanobodies (sequence shown in Example 5) in different concentrations of PEG. Proceeds are shown as follows:

1) The nanobody sample was concentrated to 5 mg/ml.

2) The samples were added into a 96-well cell culture plate with 40 µl nanobody samples per well to a final concentration of 1 mg/ml. 26.7 µl, 40 µl, 46.7 µl, 53.3 µl, 60 µl, 66.7 µl, 73.3 µl, 80 µl, 86.7 µl, 93.3 µl, 100 µl, and 106.7 µl of 30% PEG was added into columns 1 to 12, respectively, and the 161301 Buffer was added to a total volume of 200 µl. The PEG concentration gradients were 4%, 6%, 7%, 8%, 9%, 10%, 11%, 12%, 13%, 14%, 15%, and 16%, respectively.

3) The product was place at room temperature for 1 hr and OD500 nm was measured.

Figure 15:
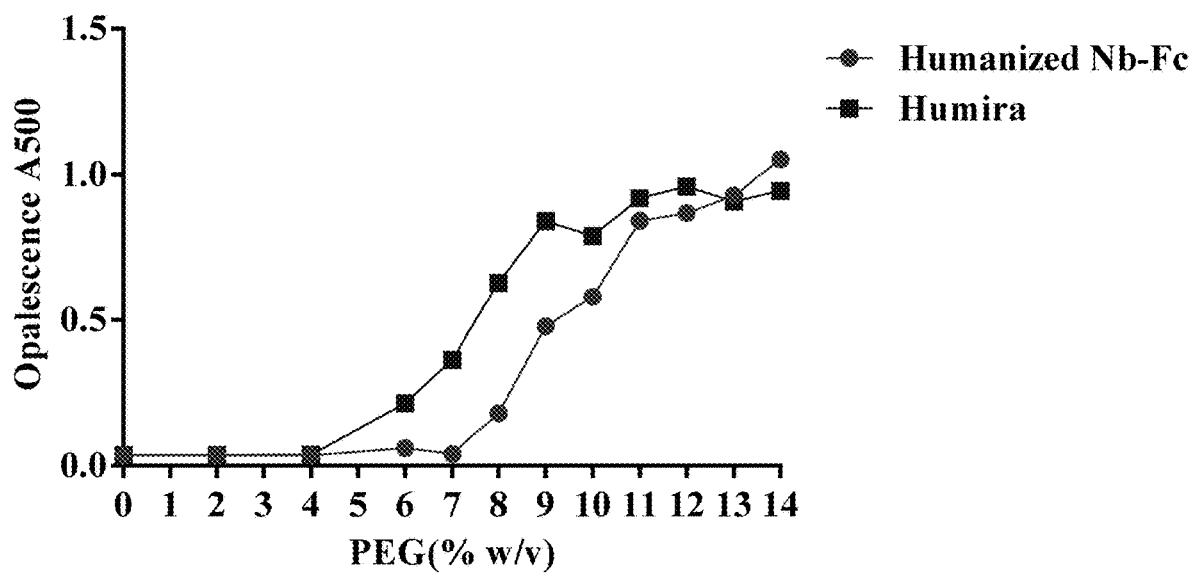
FIG. 15 shows the humanized Nb-Fc of the invention has better solubility than that of the control antibody.

The results of the study are shown in Table 6 and FIG. 15. Humanized Nb-Fc appeared turbid at 8% (w/v) PEG, while the control antibody (post-marketing agent, Humira) appeared turbid at 6% (w/v) PEG. This indicates that the humanized Nb-Fc of the present invention has superior solubility than the control nanobody.

TABLE 6

| | OD500 nm | | | | | |
|---|---|---|---|---|---|---|
| | 4% | 6% | 7% | 8% | 9% | 10% |
| humanized Nb-Fc | 0.0352 | 0.0356 | 0.0354 | 0.0602 | 0.0411 | 0.1792 |
| Humira | 0.0365 | 0.0367 | 0.0387 | 0.2144 | 0.3627 | 0.6293 |

TABLE 6-continued

| | OD500 nm | | | | | |
|---|---|---|---|---|---|---|
| | 11% | 12% | 13% | 14% | 15% | 16% |
| humanized Nb-Fc | 0.4778 | 0.5807 | 0.8418 | 0.8687 | 0.928 | 1.0514 |
| Humira | 0.8409 | 0.7891 | 0.9194 | 0.9589 | 0.9086 | 0.9444 |

Example 14. Test on Accelerated Stability

Figure 16:
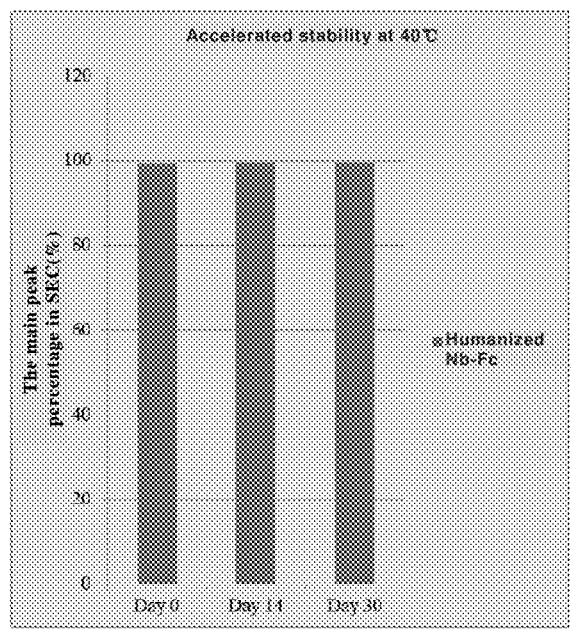
FIG. 16 shows there is no significant change in purity of the humanized Nb-Fc.

In this experiment, the long-term thermal stability of the nanobodies was evaluated by detecting changes in the purity and biological activity of the nanobodies (sequence shown in Example 5) after leaving at 40° C. for 30 days. The purity of the desired nanobodies after 0, 14 and 30 days of storage at 40° C. was determined by using SEC. As shown in Table 7 and FIG. 16, the purity of humanized Nb-Fc did not change significantly. In this experiment, the combination of accelerated stability test sample and CHO-PDL1 cells was detected by FACS method. The steps are as follows:

1) Cell preparation: CHO-PDL1 cells were counted and diluted to 2×10$^6$ cells/ml, then the cells were added into a U-bottom 96-well plate at 100 µl/well, and 50 µl of cells was added to the wells in the first column;

2) Detection steps: nanobodies were added to the first well to the final concentration of 200 nM, and mixed. 50 µl was pipetted into the second well, and so forth. The negative control is IgG Control. The product was subjected to ice bath for 20 minutes. PBS was added at 100 µl/well. The resultant was centrifuged at 400 g for 5 min to remove the supernatant and the cells were washed with PBS once. The diluted (1:100) goat anti-human IgG-PE (eBioscience) was added at 100 µl/well. The resultant was subjected to ice bath for 20 min, centrifuged at 400 g for 5 min to remove the supernatant, washed once with PBS at 100 µl/well, resuspended with 100 µl PBS and detected by FACS.

Figure 17:
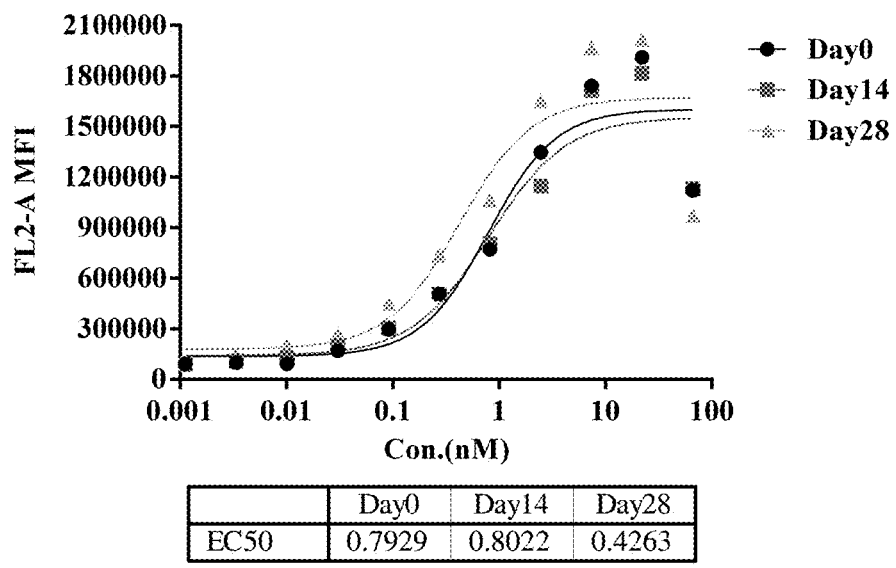
FIG. 17 shows that there is no significant change of binding between the humanized Nb-Fc and CHO-PDL1 cells.

As shown in FIG. 17, the binding of humanized Nb-Fc and CHO-PDL1 cells did not change significantly. The results show that humanized Nb-Fc has good thermal stability.

TABLE 7

| SEC (%) humanized | Day 0 | Day 14 | Day 30 |
|---|---|---|---|
| Nb-Fc | 99.55 | 99.68 | 99.71 |

All references mentioned in the present invention are incorporated herein by reference, as each of them is individually cited herein by reference. Further, it should be understood that, after reading the above contents, the skilled person can make various modifications or amendments to the present invention. All these equivalents also fall into the scope defined by the pending claims of the subject application.

The invention claimed is:

1. A variable region of a VHH chain of an anti-PD-L1 nanobody that binds to an epitope of PD-L1 comprising complementary determining regions (CDRs), wherein the CDRs consist of CDR1 of SEQ ID NO: 5, CDR2 of SEQ ID NO: 6 and CDR3 of SEQ ID NO: 7, and wherein CDR1, CDR2 and CDR3 are separated by framework regions (FRs) FR1, FR2, FR3, and FR4 of the VHH chain.

2. An anti-PD-L1 nanobody that binds to an epitope of PD-L1, comprising a VHH chain of SEQ ID NO: 8 or SEQ ID NO: 14.

3. A polynucleotide encoding a protein selected from the group consisting of
the variable region of a VHH chain of an anti-PD-L1 nanobody claim 1;
a VHH chain of an anti-PD-L1 nanobody comprising framework regions (FRs) and complementary regions (CDRs), and wherein the CDRs consist of CDR1 of SEQ ID NO: 5, CDR2 of SEQ ID NO: 6 and CDR3 of SEQ ID NO: 7, and wherein said FRs consist of
(a) FR1 of SEQ ID NO: 1, FR2 of SEQ ID NO: 2, FR3 of SEQ ID NO: 3, and FR4 of SEQ ID NO: 4; or
(b) FR1 of SEQ ID NO: 10, FR2 of SEQ ID NO: 11, FR3 of SEQ ID NO: 12, and FR4 of SEQ ID NO: 13; and
an anti-PD-L1 nanobody that binds to an epitope of PD-L1, comprising a VHH chain of SEQ ID NO: 8 or SEQ ID NO: 14.

4. The polynucleotide of claim 3, wherein said polynucleotide has a nucleotide sequence of SEQ ID NO: 9 or SEQ ID NO: 15.

5. An expression vector, which comprises the polynucleotide of claim 3.

6. A host cell, wherein the polynucleotide of claim 3 is integrated within the genome of the host cell, or which cell contains an expression vector which contains said polynucleotide.

7. A method for producing an anti-PD-L1 nanobody, comprising:
(a) culturing said host cell according to claim 6 under conditions suitable for producing nanobody, thereby obtaining a culture containing said anti-PD-L1 nanobody; and
(b) isolating or recovering said anti-PD-L1 nanobody from said culture.

8. A method for detecting a PD-L1 molecule, comprising achieving said detection by the anti-PD-L1 nanobody of claim 3.

9. A method for treating cancer, comprising administering to a subject in need thereof an effective amount of the anti-PD-L1 nanobody of claim 2.

10. A VHH chain of an anti-PD-L1 nanobody that binds to an epitope of PD-L1, wherein the VHH chain comprises framework regions (FRs) and complementary determining regions (CDRs), wherein the CDRs consist of CDR1 of SEQ ID NO: 5, CDR2 of SEQ ID NO: 6 and CDR3 of SEQ ID NO: 7, and the framework region
(a) consists of FR1 of SEQ ID NO:1, FR2 of SEQ ID NO: 2, FR3 of SEQ ID NO: 3, and FR4 of SEQ ID NO: 4; or
(b) consists of FR1 of SEQ ID NO:10, FR2 of SEQ ID NO: 11, FR3 of SEQ ID NO: 12, and FR4 of SEQ ID NO: 13.

11. An immunoconjugate comprising:
(a) the VHH chain of said anti-PD-L1 nanobody of claim 10, or an anti-PD-L1 nanobody that binds to an epitope of PD-L1, comprising a VHH chain of SEQ ID NO: 8 or SEQ ID NO: 14; and (b) a conjugating part selected from a group consisting of a detectable marker, drug, toxin, cytokine, radionuclide, and enzyme.

\* \* \* \* \*

SEQUENCE LISTING

<160> NUMBER OF SEQ ID NOS: 15

<210> SEQ ID NO 1
<211> LENGTH: 25
<212> TYPE: PRT
<213> ORGANISM: Camelus Linnaeus

<400> SEQUENCE: 1

Gln Val Gln Leu Gln Glu Ser Gly Gly Gly Ser Val Gln Ala Gly Gly
1               5                   10                  15

Ser Leu Arg Leu Ser Cys Gln Ala Ser
            20                  25

<210> SEQ ID NO 2
<211> LENGTH: 15
<212> TYPE: PRT
<213> ORGANISM: Camelus Linnaeus

<400> SEQUENCE: 2

Trp Phe Arg Gln Ala Pro Gly Lys Gln Arg Glu Gly Val Ala Ala
1               5                   10                  15

<210> SEQ ID NO 3
<211> LENGTH: 38
<212> TYPE: PRT
<213> ORGANISM: Camelus Linnaeus

<400> SEQUENCE: 3

Ser Tyr Ser Asp Ser Val Lys Gly Arg Phe Thr Ile Ser Leu Gly Asn
1               5                   10                  15

Ala Lys Asn Thr Leu Tyr Leu Glu Met Asn Ser Leu Lys Pro Glu Asp
            20                  25                  30

Thr Ala Met Tyr Tyr Cys
            35

<210> SEQ ID NO 4
<211> LENGTH: 11
<212> TYPE: PRT
<213> ORGANISM: Camelus Linnaeus

<400> SEQUENCE: 4

Trp Gly Gln Gly Thr Gln Val Thr Val Ser Ser
1               5                   10

<210> SEQ ID NO 5
<211> LENGTH: 10
<212> TYPE: PRT
<213> ORGANISM: Camelus Linnaeus

<400> SEQUENCE: 5

Ala Tyr Thr Ile Ser Arg Asn Ser Met Gly
1               5                   10

<210> SEQ ID NO 6
<211> LENGTH: 7
<212> TYPE: PRT
<213> ORGANISM: Camelus Linnaeus

<400> SEQUENCE: 6

Ile Glu Ser Asp Gly Ser Thr
1               5

<210> SEQ ID NO 7
<211> LENGTH: 26
<212> TYPE: PRT
<213> ORGANISM: Camelus Linnaeus

<400> SEQUENCE: 7

Ala Ala Pro Lys Val Gly Leu Gly Pro Arg Thr Ala Leu Gly His Leu
1               5                   10                  15
Ala Phe Met Thr Leu Pro Ala Leu Asn Tyr
            20                  25

<210> SEQ ID NO 8
<211> LENGTH: 132
<212> TYPE: PRT
<213> ORGANISM: Camelus Linnaeus

<400> SEQUENCE: 8

Gln Val Gln Leu Gln Glu Ser Gly Gly Gly Ser Val Gln Ala Gly Gly
1               5                   10                  15
Ser Leu Arg Leu Ser Cys Gln Ala Ser Ala Tyr Thr Ile Ser Arg Asn
            20                  25                  30
Ser Met Gly Trp Phe Arg Gln Ala Pro Gly Lys Gln Arg Glu Gly Val
        35                  40                  45
Ala Ala Ile Glu Ser Asp Gly Ser Thr Ser Tyr Ser Asp Ser Val Lys
    50                  55                  60
Gly Arg Phe Thr Ile Ser Leu Gly Asn Ala Lys Asn Thr Leu Tyr Leu
65                  70                  75                  80
Glu Met Asn Ser Leu Lys Pro Glu Asp Thr Ala Met Tyr Tyr Cys Ala
                85                  90                  95
Ala Pro Lys Val Gly Leu Gly Pro Arg Thr Ala Leu Gly His Leu Ala
            100                 105                 110
Phe Met Thr Leu Pro Ala Leu Asn Tyr Trp Gly Gln Gly Thr Gln Val
        115                 120                 125
Thr Val Ser Ser
    130

<210> SEQ ID NO 9
<211> LENGTH: 396
<212> TYPE: DNA
<213> ORGANISM: Camelus Linnaeus

<400> SEQUENCE: 9
caggtgcagc tgcaggagtc tgggggaggc tcggtacagg ctggagggtc tctgagactc      60
tcctgtcaag cctctgcata caccatcagt agaaactcca tgggctggtt ccgccaggct     120
ccagggaagc agcgcgaggg ggtcgcagct attgaaagtg atggcagcac aagttactca     180
gactccgtca aggccgatt caccatctcc ttaggcaacg ccaagaacac tctgtatctg     240
gaaatgaaca gcctgaaacc tgaggacact gccatgtact actgcgcggc gccgaaggtg     300
ggcctgggcc ctaggactgc tttaggccat cttgcattta tgaccttacc agccctaaac     360
tactggggcc agggaacccca ggtcaccgtc tcctca                              396

<210> SEQ ID NO 10
<211> LENGTH: 25
<212> TYPE: PRT
<213> ORGANISM: artificial sequence
<220> FEATURE:
<223> OTHER INFORMATION: humanized FR1

```
<400> SEQUENCE: 10

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 11
<211> LENGTH: 15
<212> TYPE: PRT
<213> ORGANISM: artificial sequence
<220> FEATURE:
<223> OTHER INFORMATION: humanized FR2

<400> SEQUENCE: 11

Trp Phe Arg Gln Ala Pro Gly Lys Gly Leu Glu Gly Val Ala Ala
1               5                   10                  15

<210> SEQ ID NO 12
<211> LENGTH: 38
<212> TYPE: PRT
<213> ORGANISM: artificial sequence
<220> FEATURE:
<223> OTHER INFORMATION: humanized FR3

<400> SEQUENCE: 12

Ser Tyr Ser Asp Ser Val Lys Gly Arg Phe Thr Ile Ser Leu Asp Asn
1               5                   10                  15

Ser Lys Asn Thr Leu Tyr Leu Glu Met Asn Ser Leu Arg Ala Glu Asp
            20                  25                  30

Thr Ala Val Tyr Tyr Cys
                35

<210> SEQ ID NO 13
<211> LENGTH: 11
<212> TYPE: PRT
<213> ORGANISM: artificial sequence
<220> FEATURE:
<223> OTHER INFORMATION: humanized FR4

<400> SEQUENCE: 13

Trp Gly Gln Gly Thr Leu Val Thr Val Ser Ser
1               5                   10

<210> SEQ ID NO 14
<211> LENGTH: 132
<212> TYPE: PRT
<213> ORGANISM: artificial sequence
<220> FEATURE:
<223> OTHER INFORMATION: humanized VHH

<400> SEQUENCE: 14

Gln Val Gln Leu Gln Glu Ser Gly Gly Gly Leu Val Gln Pro Gly Gly
1               5                   10                  15

Ser Leu Arg Leu Ser Cys Ala Ala Ser Ala Tyr Thr Ile Ser Arg Asn
            20                  25                  30

Ser Met Gly Trp Phe Arg Gln Ala Pro Gly Lys Gly Leu Glu Gly Val
        35                  40                  45

Ala Ala Ile Glu Ser Asp Gly Ser Thr Ser Tyr Ser Asp Ser Val Lys
    50                  55                  60

Gly Arg Phe Thr Ile Ser Leu Asp Asn Ser Lys Asn Thr Leu Tyr Leu
65                  70                  75                  80
```

```
Glu Met Asn Ser Leu Arg Ala Glu Asp Thr Ala Val Tyr Tyr Cys Ala
                85                  90                  95

Ala Pro Lys Val Gly Leu Gly Pro Arg Thr Ala Leu Gly His Leu Ala
            100                 105                 110

Phe Met Thr Leu Pro Ala Leu Asn Tyr Trp Gly Gln Gly Thr Leu Val
        115                 120                 125

Thr Val Ser Ser
    130

<210> SEQ ID NO 15
<211> LENGTH: 396
<212> TYPE: DNA
<213> ORGANISM: artificial sequence
<220> FEATURE:
<223> OTHER INFORMATION: humanized VHH

<400> SEQUENCE: 15
caggtgcagc tgcaggagag cggcggcggc ctggtgcagc ccggcggcag cctgaggctg      60
agctgcgccg ccagcgccta caccatcagc aggaacagca tgggctggtt caggcaggcc     120
cccggcaagg gcctggaggg cgtggccgcc atcgagagcg acggcagcac cagctacagc     180
gacagcgtga agggcaggtt caccatcagc ctggacaaca gcaagaacac cctgtacctg     240
gagatgaaca gcctgagggc cgaggacacc gccgtgtact actgcgccgc ccccaaggtg     300
ggcctgggcc ccaggaccgc cctggccac ctggccttca tgaccctgcc cgccctgaac     360
tactggggcc agggcaccct ggtgaccgtg agcagc                               396
```